United States Patent
Ventre et al.

(10) Patent No.: US 6,547,789 B1
(45) Date of Patent: Apr. 15, 2003

(54) HOLDING APPARATUS FOR THE SPINAL COLUMN

(75) Inventors: Carlo Ventre, Turbenthal (CH); Cosimo Donno, Winterthur (CH); Armin Studer, Steinhausen (CH); Onur Adali, Tagelswangen (CH); André Lobsiger, Winterthur (CH); Daniel Hug, Weisslingen (CH); Raffael Berani, Uster (CH); Daniel Ambühl, Embrach (CH)

(73) Assignee: Sulzer Orthopedics Ltd., Baar (CH)

( * ) Notice: Subject to any disclaimer, the term of this patent is extended or adjusted under 35 U.S.C. 154(b) by 0 days.

(21) Appl. No.: 09/580,016

(22) Filed: May 26, 2000

(30) Foreign Application Priority Data

Jul. 2, 1999 (EP) .............................. 99810579

(51) Int. Cl.⁷ .............................. A61B 17/70
(52) U.S. Cl. .......................... 606/61; 606/72
(58) Field of Search .............. 606/60, 61, 54, 606/72, 73

(56) References Cited

U.S. PATENT DOCUMENTS 5,257,993 A * 11/1993 Asher et al. ............ 606/61
5,476,462 A 12/1995 Allard
5,624,441 A * 4/1997 Sherman et al. ........ 606/61
5,630,817 A 5/1997 Rokegem
5,658,284 A * 8/1997 Sebastian et al. ....... 606/61
6,077,262 A 6/2000 Schlaepfer

FOREIGN PATENT DOCUMENTS

| DE | 94 03 231 | 4/1994 |
| EP | 0 535 623 A1 | 4/1993 |
| FR | 2 624 720 A1 | 6/1989 |
| FR | 2780269 | 12/1999 |
| WO | WO 96/21396 | 7/1996 |

* cited by examiner

*Primary Examiner*—David O. Reip
(74) *Attorney, Agent, or Firm*—Townsend and Townsend and Crew LLP

(57) ABSTRACT

A holding apparatus for the vertebra of a spinal column. It furthermore has a mount for a bar which is provided at the side of the holding apparatus which faces away from a clamping screw. The clamping screw of the holding apparatus produces a rigid connection of the holding apparatus to the bar which is located in the mount. The apparatus retains the bar in the mount and can be brought into connection with the holding apparatus so as to temporarily retain in the mount a bar which is introduced into the mount until the holding apparatus is fixed to the bar by way of a rigid connection.

3 Claims, 12 Drawing Sheets

Figure 1:
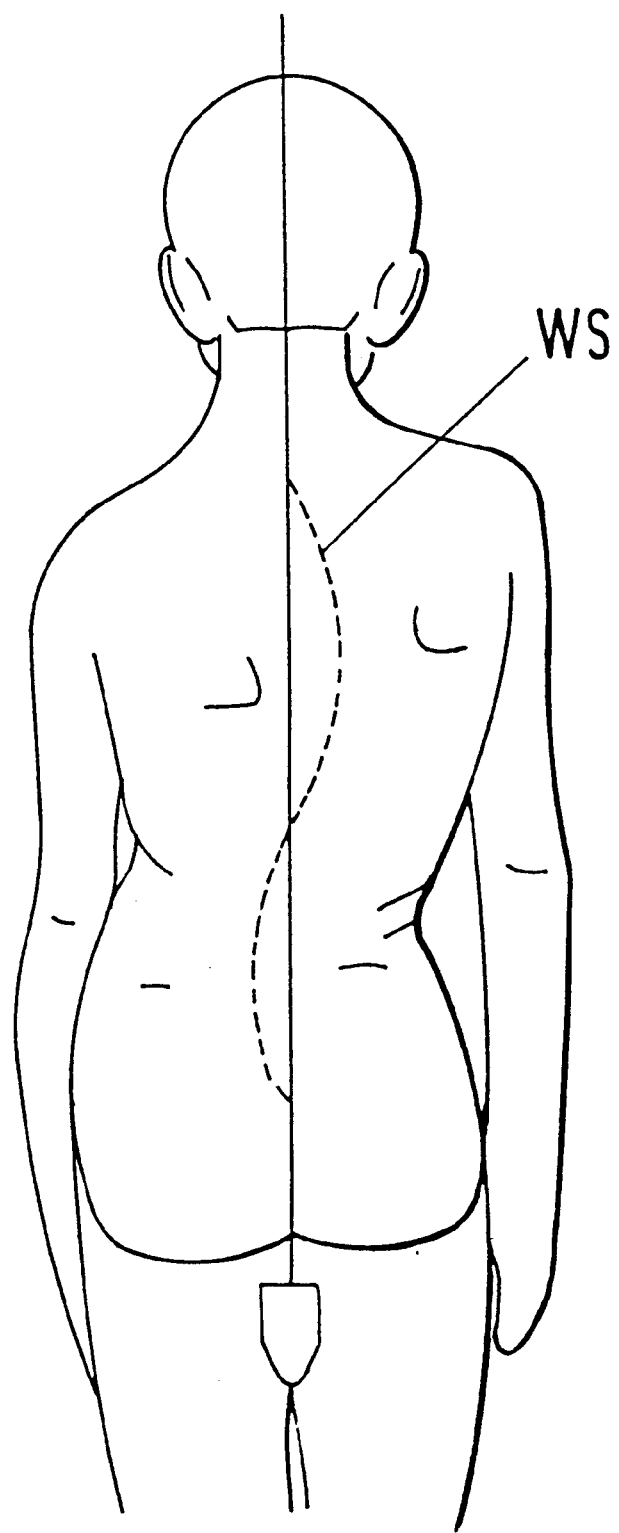

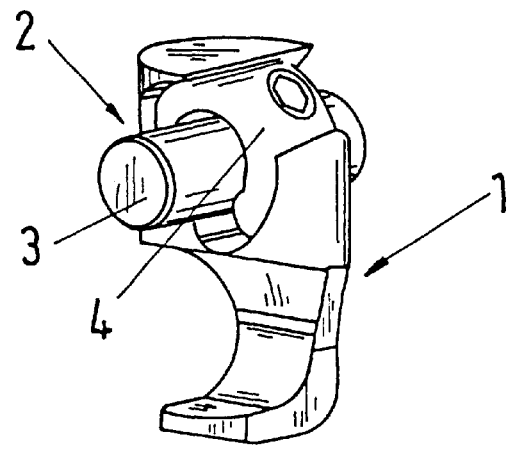
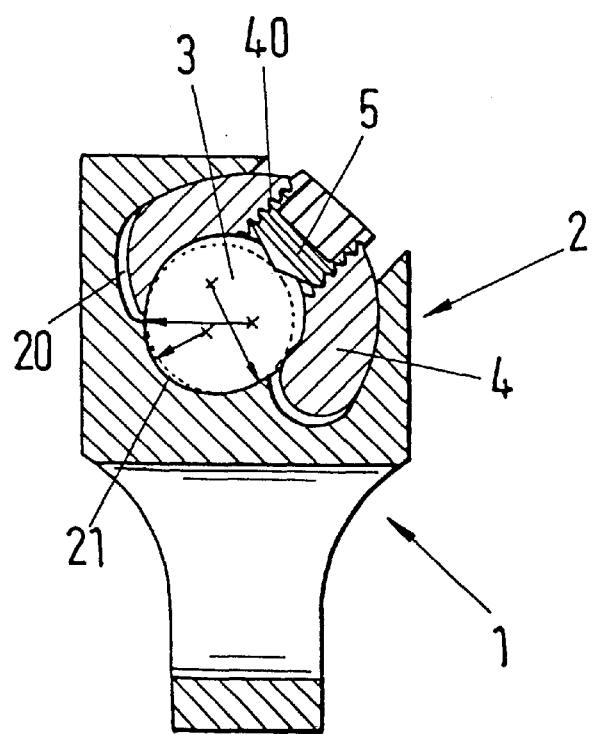
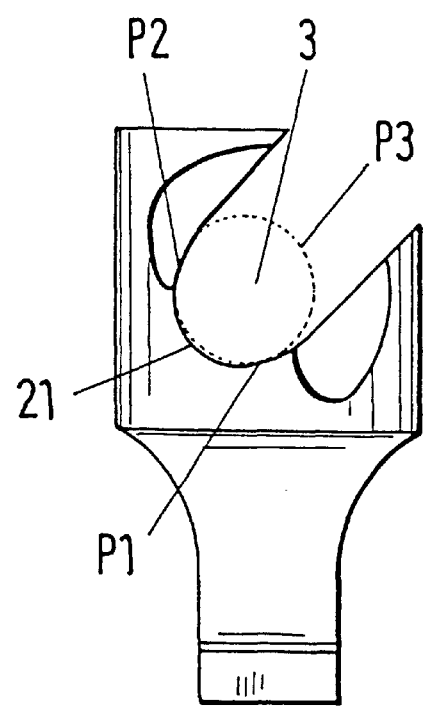

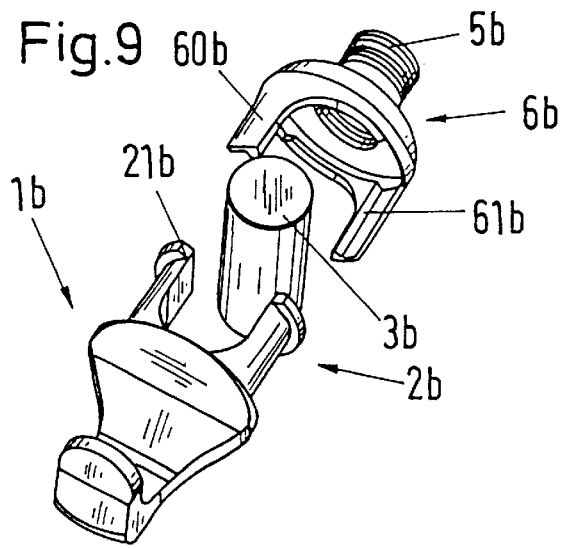
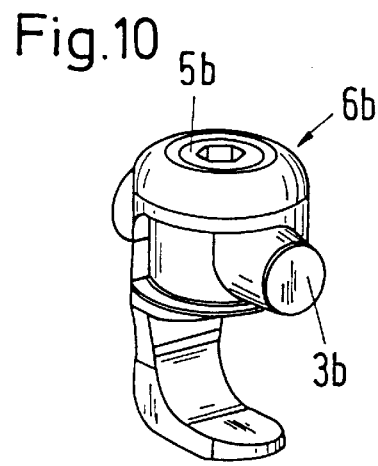
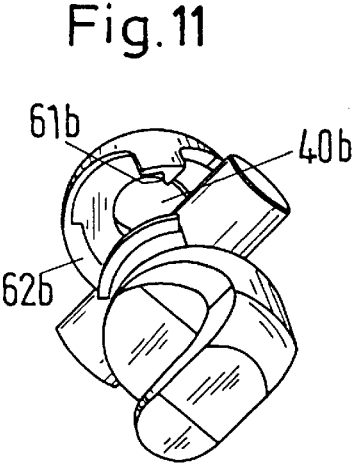
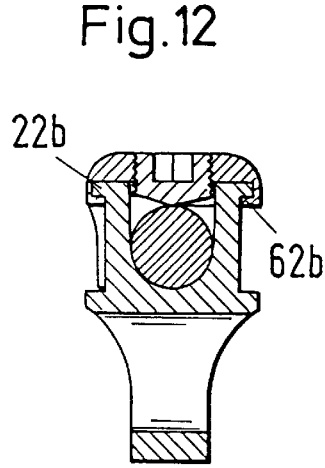
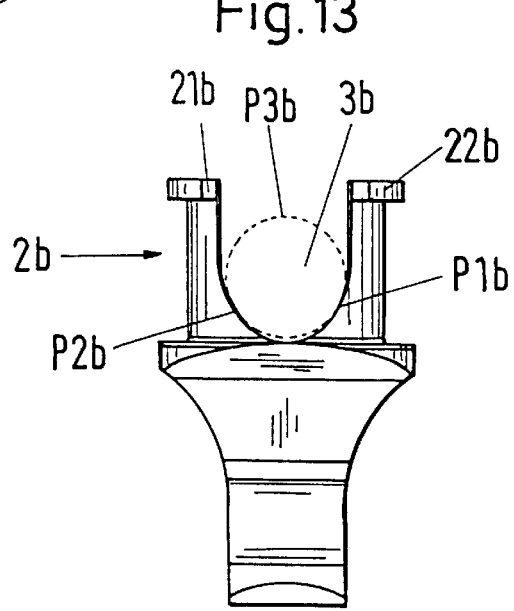

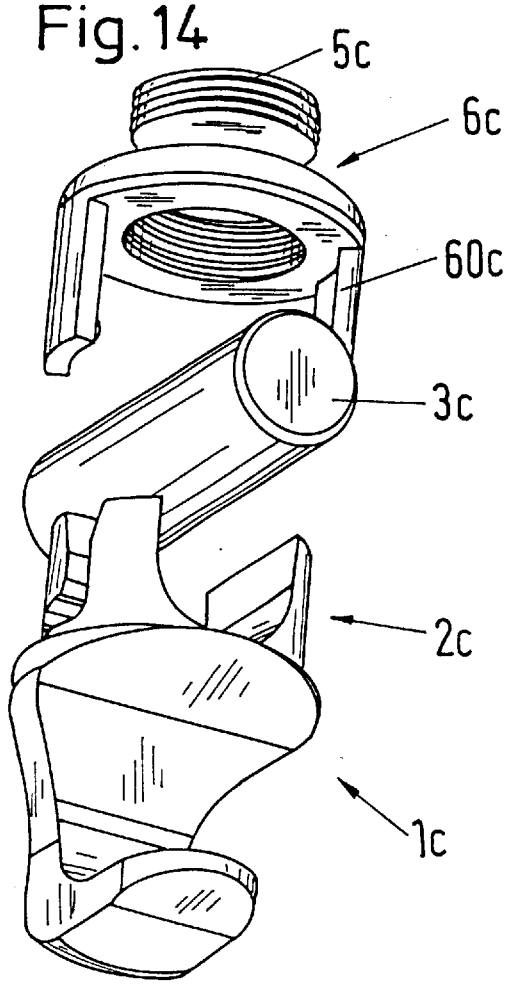
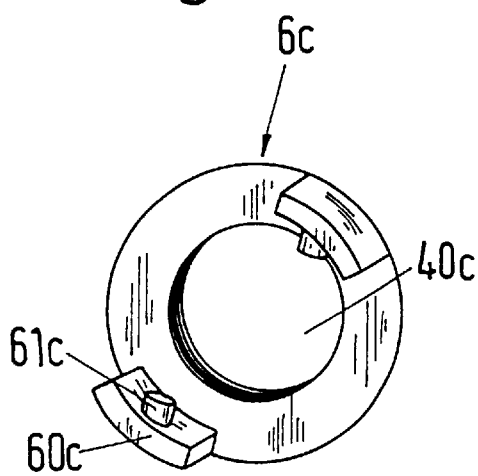
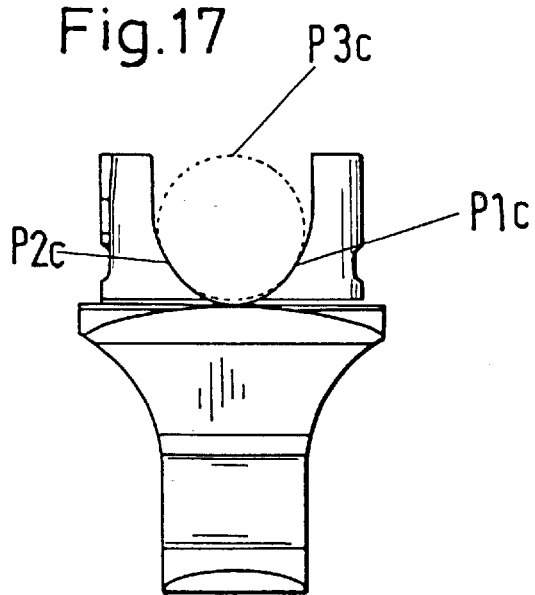
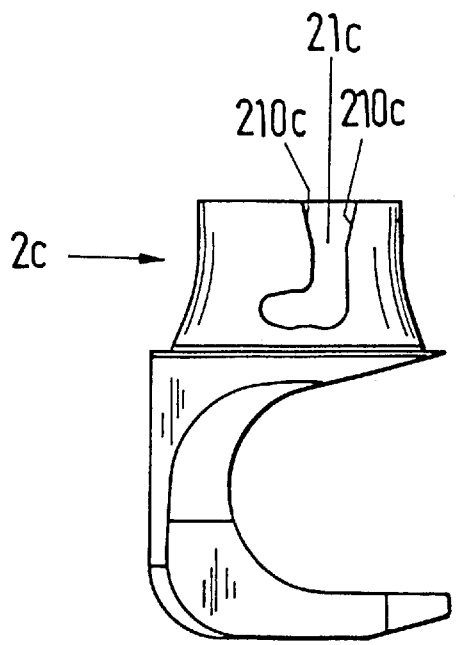

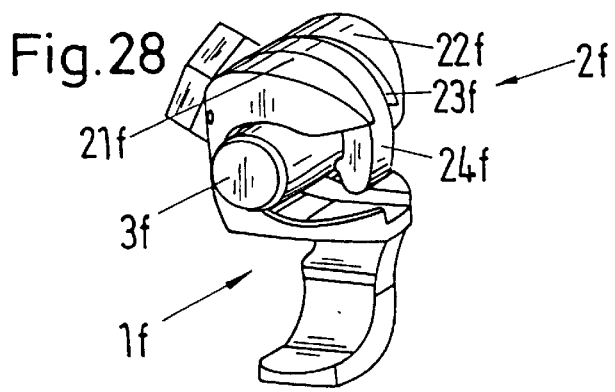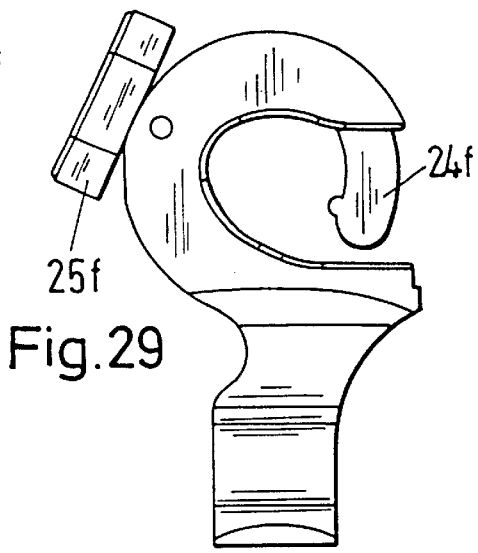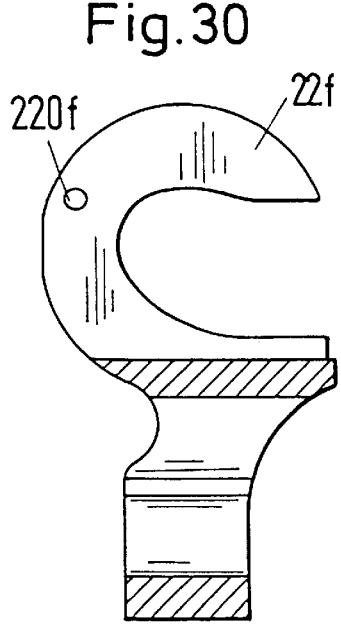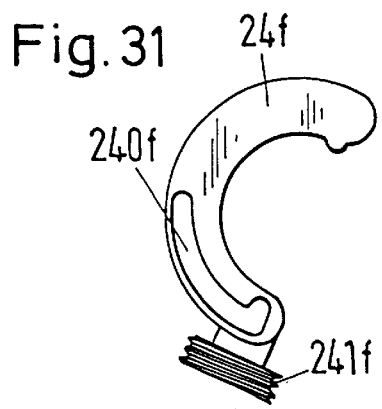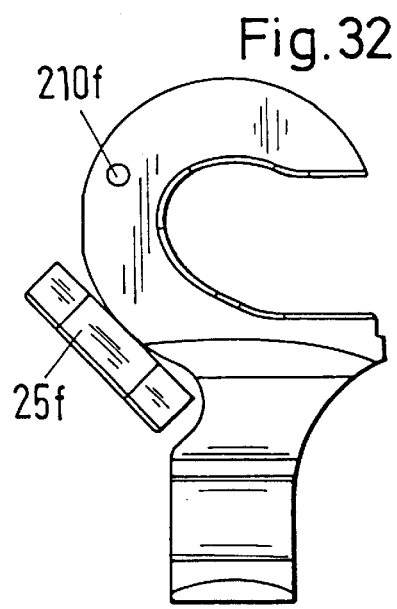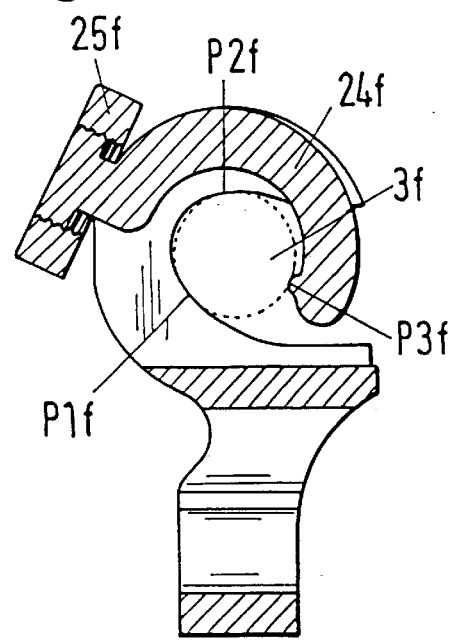

HOLDING APPARATUS FOR THE SPINAL COLUMN

The invention relates to a holding apparatus for the spinal column in accordance with the preamble of the independent patent claim.

Holding apparatuses of this kind are used in deformations of the human spinal column. The principle is that the holding apparatuses are secured at a plurality of vertebrae and are connected to one another by means of one or more bars, through which the spinal column is mechanically held in a desired position.

Scoliosis is for example such a deformation of the spinal column. A lateral bending of the spinal column, which can also be entailed with a torsion of the individual vertebrae, is designated as a scoliosis. A distinction is made in principle between a total or C-shaped scoliosis (curvature of the spinal column to one side without a counter-curvature), a compound or S-shaped scoliosis (curvature with counter-curvature) and a triple scoliosis (curvature with a compensatory counter-curvature in the cranial and the caudal direction). A compound or S-shaped scoliosis is for example schematically indicated in FIG. 1. The broken line indicates the S-shaped form of the spinal column WS.

In an operational correction of the spinal column holding apparatuses, which e.g. have a hook, are secured to the vertebrae. The hooks grip beneath or behind respectively the lamina of the respective vertebra and hook in there, but they can however also grip on at the pedicles or at the respective transverse process (spine of a vertebra). Typically a holding apparatus is first secured at one vertebra each at the two ends of the region of the deformation of the spinal column. The holding apparatuses have a mount for a bar at their end which faces away from the hook. The bar has a predetermined shape which causes the spinal column to have a desired course when the individual vertebrae are connected to the bar in the region of the deformation by means of a holding apparatus.

Holding apparatuses are then likewise secured at the vertebrae in the region of the deformation of the spinal column. After the securing of a holding apparatus of this kind at the respective vertebra in the region of the deformation, the holding apparatus together with the vertebra is drawn towards the bar until the mount of the holding apparatus then takes up the bar. Then the respective vertebra is located in its desired position. The holding apparatus must now be firmly connected to the bar, since the spinal column naturally attempts to arrive back into the position of the deformation. This is somewhat difficult for the operating surgeon to accomplish since he must on the one hand carry out a lateral movement toward the bar of the vertebra together with the holding apparatus which is secured thereto, and must on the other hand possibly also effect a movement of the vertebra with the holding apparatus in the dorsal or ventral direction, and finally also possibly a longitudinal displacement of the vertebra together with the holding apparatus along the bar (thus practically a displacement in the cranial or caudal direction). Once he has carried out this movement of the vertebra together with the holding apparatus which is secured thereto, he must on the one hand hold the vertebra in the desired position and on the other hand fix the holding apparatus to the bar at the same time. This is connected with the above described difficulties in the handling for the operating surgeon since of course the spinal column attempts to restore the original (deformed) state.

An object of the invention is thus to propose a holding apparatus which facilitates the handling for the operating surgeon during the securing of the holding apparatus at the bar.

This object is satisfied by a holding apparatus such as is characterized by the features of the independent patent claim. Particularly advantageous embodiments result from the subordinate patent claims and from the following description of the exemplary embodiments which are illustrated in the drawings respectively.

The holding apparatus in accordance with the invention has means for retaining the bar in the mount which are executed in such a manner and can be brought into connection with the holding apparatus in such a manner that they temporarily retain in the mount a bar which is introduced into the mount until the holding apparatus is fixed to the bar with the help of the means for producing the rigid connection. This means that the operating surgeon can achieve a temporary fixing of the holding apparatus and thus of the corresponding vertebra in a simple manner although the spinal column attempts to restore the state of the deformation. Nevertheless the holding apparatus remains displaceable on the bar in the axial direction of the latter.

The operating surgeon can thus first bring a vertebra from a region in which a deformation of the spinal column is present into the desired position and then connect the holding apparatus rigidly to the bar so that at first a vertebra or the holding apparatus which is connected thereto respectively is rigidly connected to the bar. Alternatively, the operating surgeon can also first temporarily secure a plurality of vertebrae from the region in which the deformation of the spinal column is present to the bar so that the former are still displaceable in the axial direction on the bar and only then determine the final position of the respective vertebra. This has the advantage that the holding apparatuses and the vertebra which are secured thereto are still "longitudinally displaceable" relative to one another so that the final position of the holding apparatuses and the vertebrae which are secured thereto need be determined only after the correction of an entire region of the spinal column. This then takes place in the same way through the rigid connection of the holding apparatus to the bar.

The mount for the bar is advantageously designed in such a manner that the means for retaining the bar can be brought into connection with the mount itself. This region, that is, the mount itself, is still the best accessible for the surgeon during the operation after the securing of the holding apparatus at the vertebra (e.g. by means of a hook or a pedicle screw).

Furthermore, the means for retaining the bar can advantageously be designed in such a manner that they receive a clamping screw which form the means for producing the rigid connection of the holding apparatus to the bar. This kind of rigid fixing of the holding apparatus to the bar can be realized simply and without a great effort and results in a reliable connection of the holding apparatus to the bar.

The mount for the bar and the means for producing the rigid connection of the holding apparatus to the bar can preferably be executed in such a manner that they form a three point support. This kind of support is well defined and particularly reliable.

For the temporary fixing, a plurality of variants advantageously present themselves. One variant provides for example that the means for retaining the bar comprise an element which enters into a snap connection with the holding apparatus or with the bar.

Another variant provides that the means for retaining the bar comprise a cover which is executed in such a manner that it enters into a connection of the manner of a bayonet lock with corresponding means at the holding apparatus.

Yet another variant provides that the means for retaining the bar comprise a cover which can be pushed onto the mount in the axial direction and which has a through-going threaded bore through which a clamping screw can be screwed through completely; and that the mount is designed to be elastically deformable in that end region of its wall which faces the cover. There the wall has projections which is in engagement after a deformation with projections which are correspondingly formed at the cover. The bar is snapped in in the mount in this variant so that it can not inadvertently escape.

Still another variant provides that the means for retaining the bar comprise a sickle shaped finger which is pivotally arranged in a cut-out between two stationary fingers which are formed in the manner of a hook at the mount. At the respective surface of the stationary hook-like finger pointing to the movable finger, a pin which points to the movable finger is in each case provided. This pin engages into a corresponding cut-out which is provided at the movable finger in the respective surface which points to the stationary finger. In this the movable finger has an extension which projects outwardly beyond the cut-out and which is provided with a thread onto which a nut can be screwed. Thus through pivoting the finger the bar can at first be temporarily retained in the mount. Then the final rigid connection of the holding apparatus to the bar can be effected through a tightening of the nut.

Figure 5:
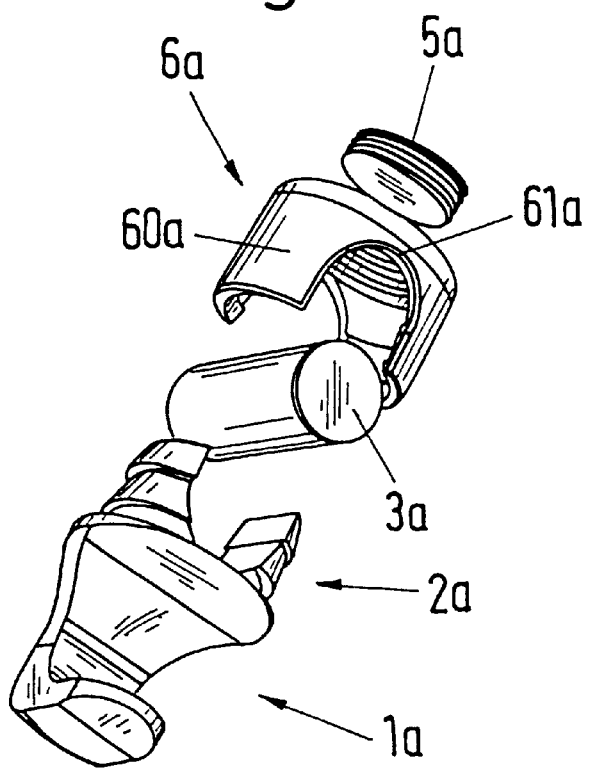
Figure 6:
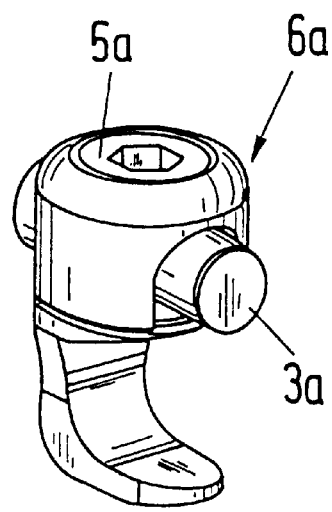
Figure 8:
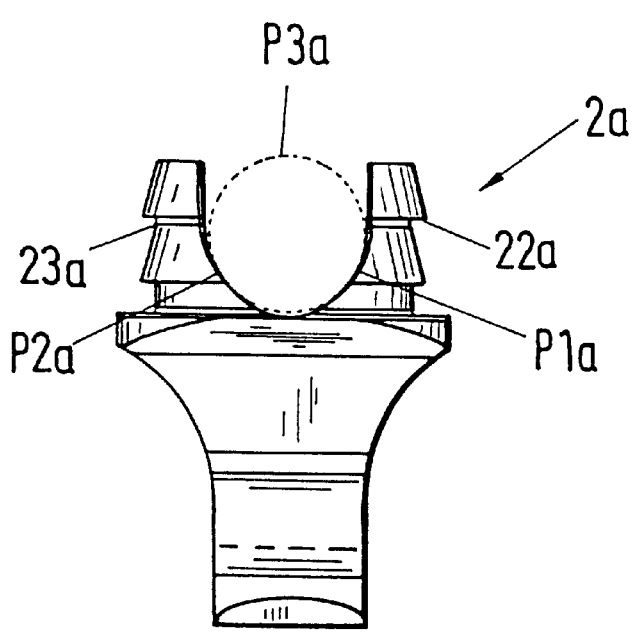
Figure 7:
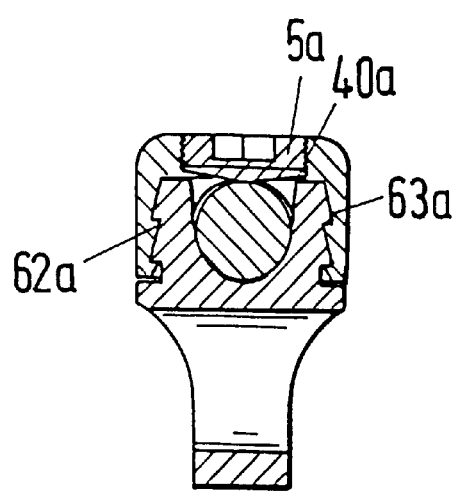
Figure 18:
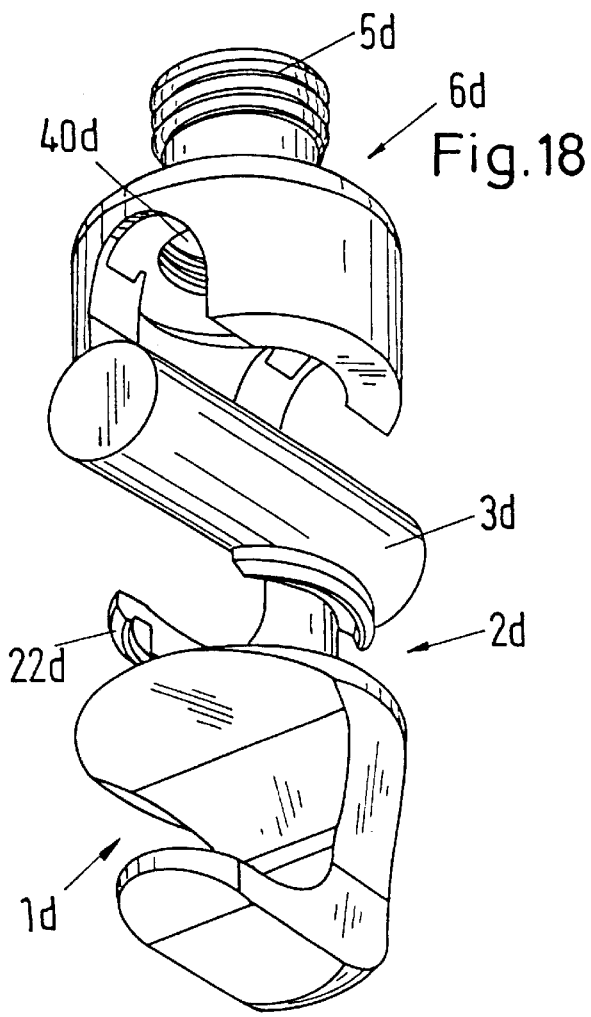
Figure 19:
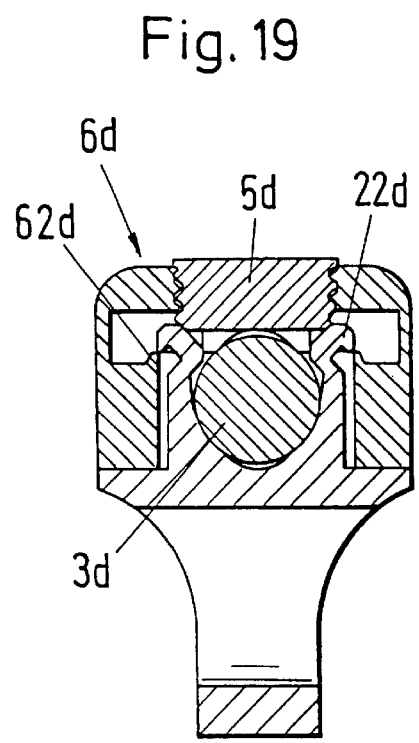
Figure 20:
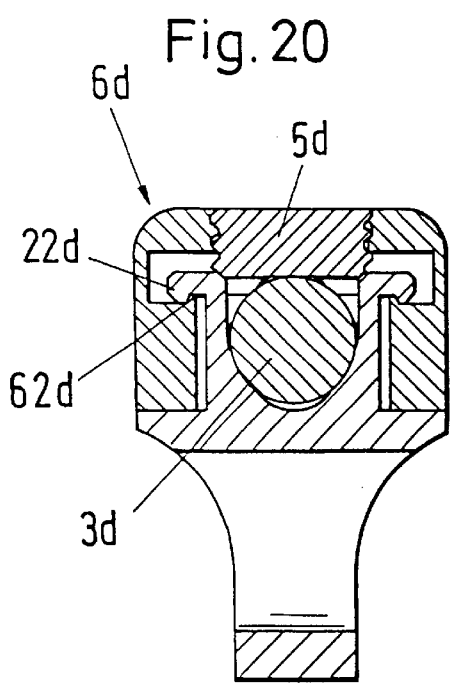
Figure 21:
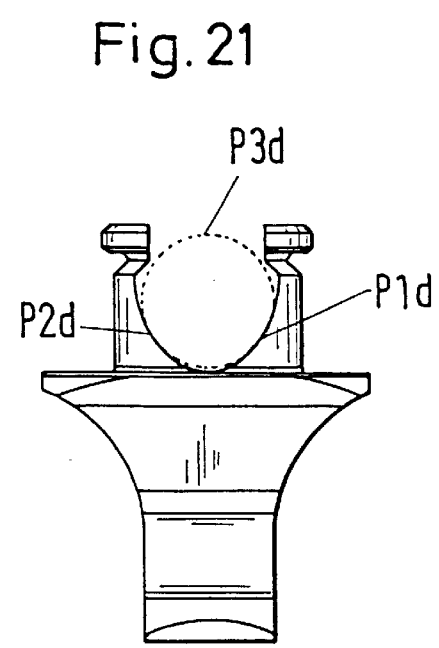
Figure 22:
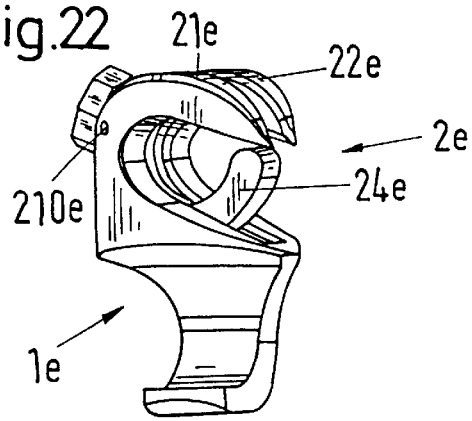
Figure 23:
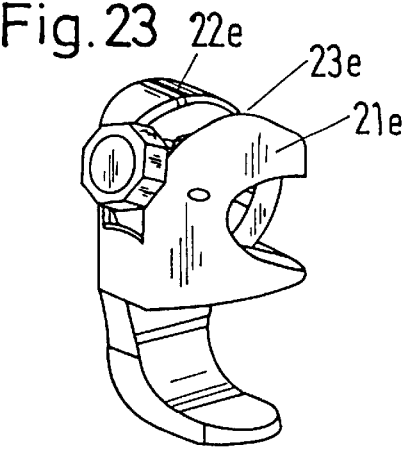
Figure 24:
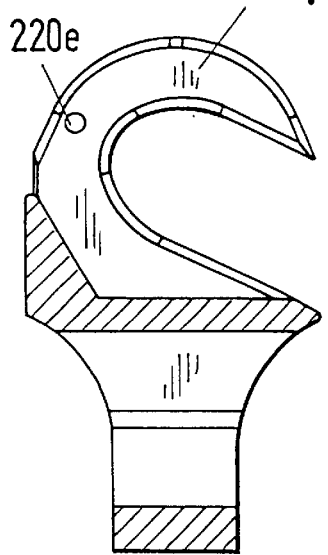
Figure 25:
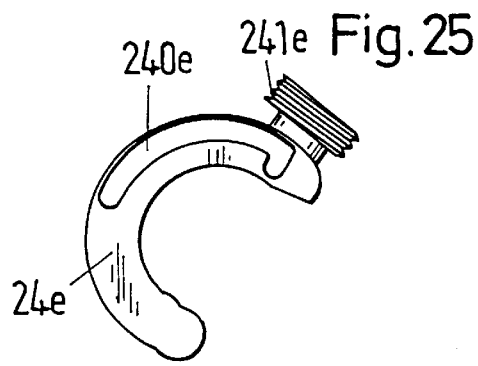
Figure 26:
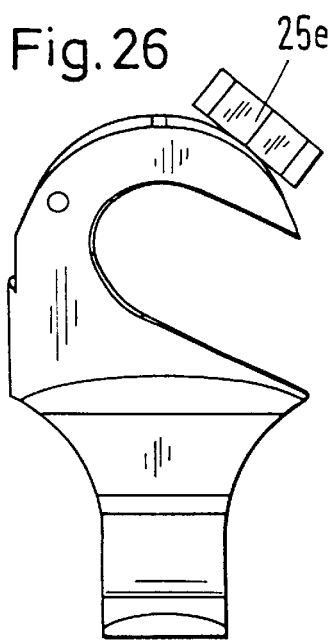
Figure 27:
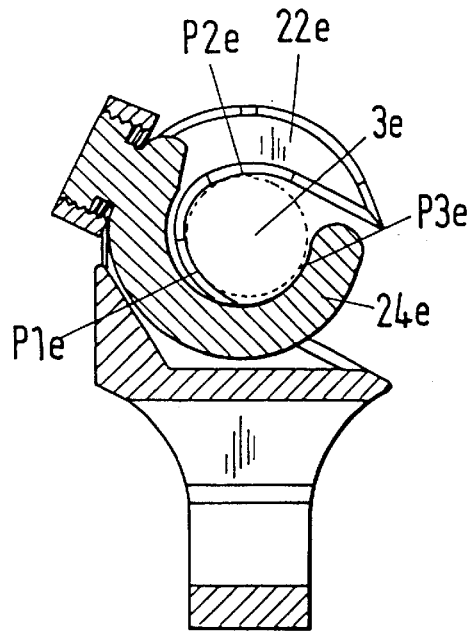
Figure 34:
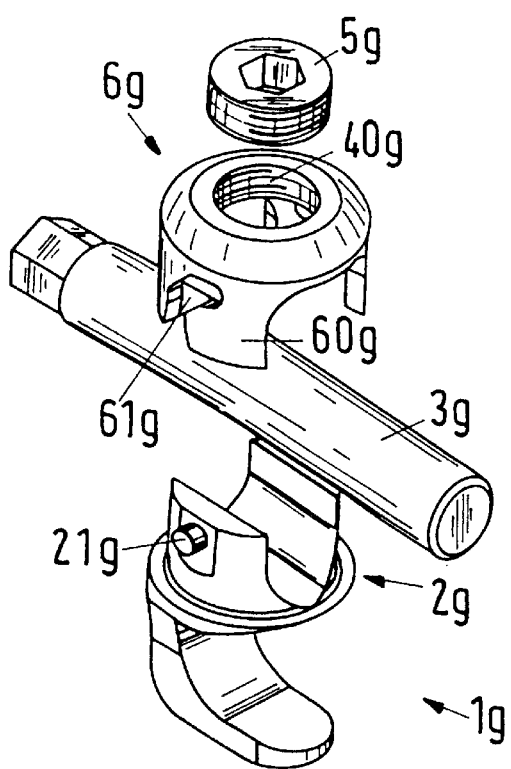
Figure 35:
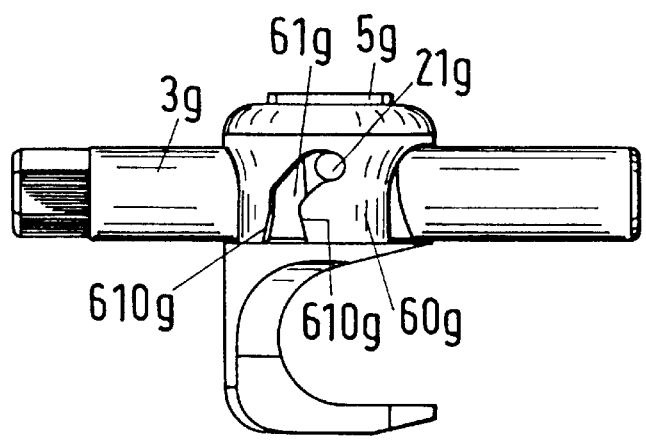
Figure 36:
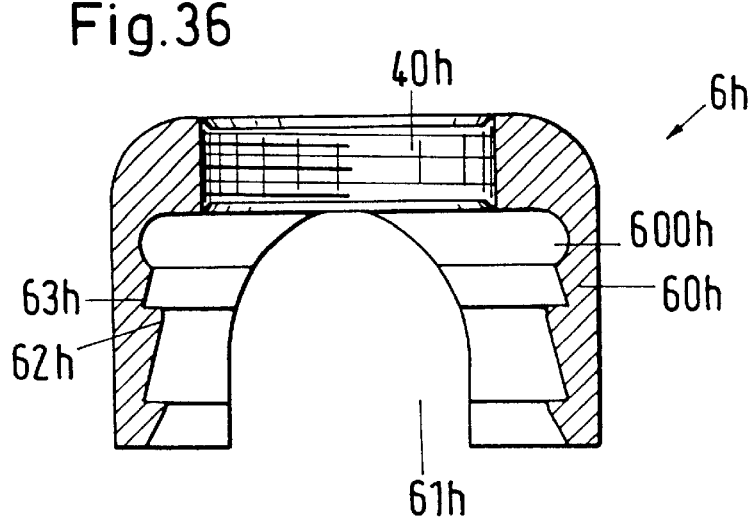
Figure 37:
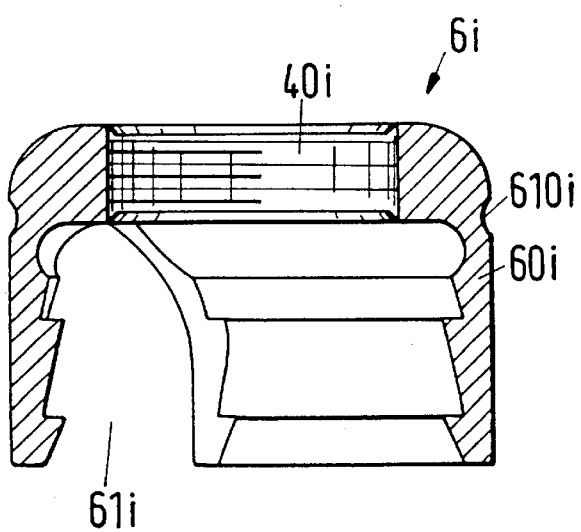
Figure 38:
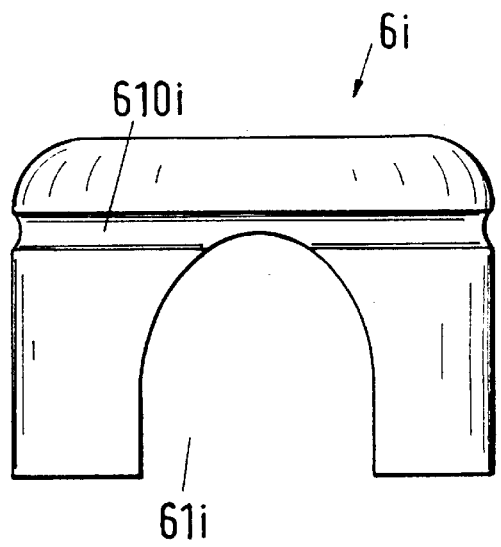
Figure 39:
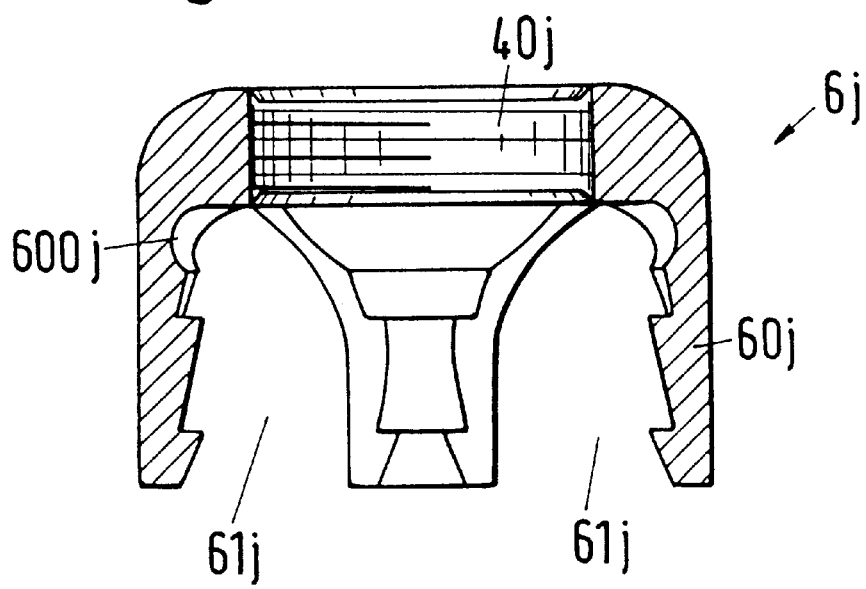
Figure 40:
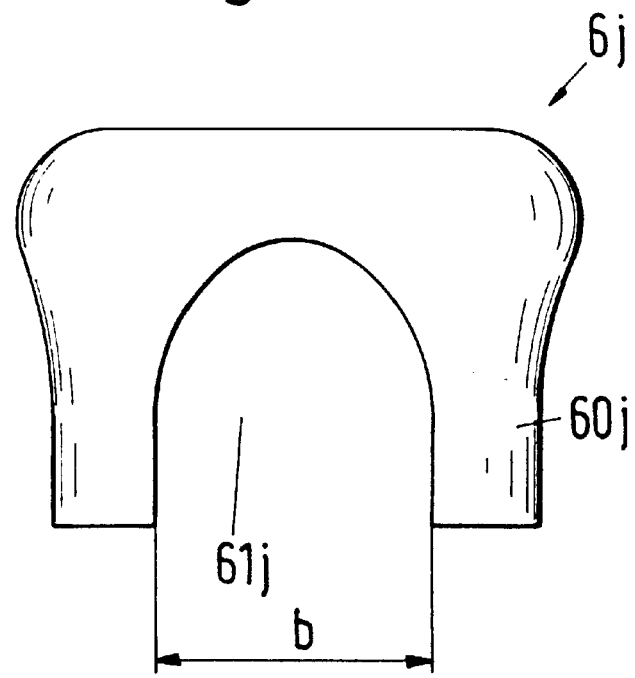
Figure 41:
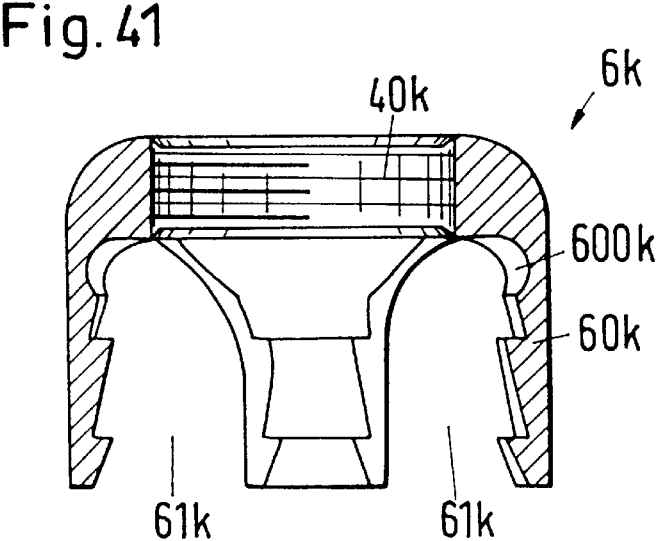
Figure 42:
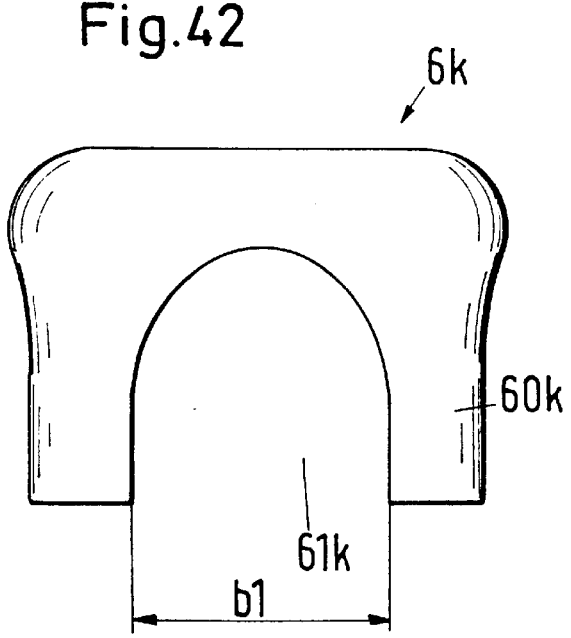
Figure 43:
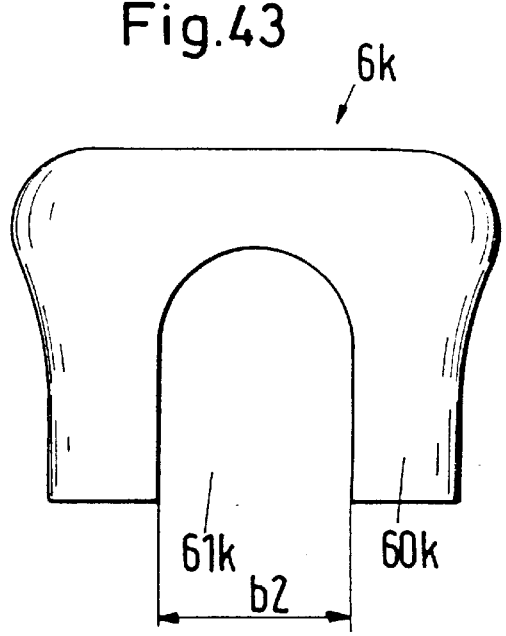

Further particularly advantageous embodiments result from the description of the following exemplary embodiments of a holding apparatus in accordance with the invention. Shown, partly in schematic illustration and/or in section, are:

FIG. 1 an illustration of a compound or S-shaped scoliosis,

FIGS. 2–4 a first exemplary embodiment of a holding apparatus in accordance with the invention, and indeed FIG. 2 a perspective view of this holding apparatus when assembled FIG. 3 a sectional illustration of this holding apparatus when assembled FIG. 4 a schematic illustration for explaining the three point support FIGS. 5–8 a second exemplary embodiment of a holding apparatus in accordance with the invention, and indeed FIG. 5 a perspective exploded view of this holding apparatus, FIG. 6 a perspective illustration of this holding apparatus when assembled, FIG. 7 a sectional illustration of this holding apparatus when assembled, FIG. 8 a schematic illustration for explaining the three point support FIGS. 9–13 a third exemplary embodiment of a holding apparatus in accordance with the invention, and indeed FIG. 9 a perspective exploded view of this holding apparatus, FIG. 10 a perspective illustration of this holding apparatus when assembled, FIG. 11 a perspective exploded view of this holding apparatus in a view from below, FIG. 12 a sectional illustration of this holding apparatus when assembled, FIG. 13 a schematic illustration for explaining the three point support FIGS. 14–17 a fourth exemplary embodiment of a holding apparatus in accordance with the invention, and indeed FIG. 14 a perspective exploded view of this holding apparatus, FIG. 15 a perspective view of the cover of this holding apparatus from below, FIG. 16 a perspective view of this holding apparatus without the cover from the side, FIG. 17 a schematic illustration for explaining the three point support, FIGS. 18–21 a fifth exemplary embodiment of a holding apparatus in accordance with the invention, and indeed FIG. 18 a perspective exploded view of this holding apparatus, FIG. 19 a sectional illustration of this holding apparatus with an only slightly screwed in clamping screw, FIG. 20 a sectional illustration of this holding apparatus with a completely screwed in clamping screw, FIG. 21 a schematic illustration for explaining the three point support, FIGS. 22–27 a sixth exemplary embodiment of a holding apparatus in accordance with the invention, and indeed FIG. 22 a perspective view of this holding apparatus from the front, when assembled, FIG. 23 a perspective view of this holding apparatus laterally from the front, when assembled, FIG. 24 a sectional illustration of this holding apparatus without the movable finger, FIG. 25 the movable finger in a side view, FIG. 26 a view of this holding apparatus from the front, with pivoted out finger, FIG. 27 a sectional illustration of this holding apparatus with pivoted in finger, for explaining the three point support, FIGS. 28–33 a seventh exemplary embodiment of a holding apparatus in accordance with the invention, and indeed FIG. 28 a perspective view of this holding apparatus from the front, when assembled, FIG. 29 a view of this holding apparatus from the front, with pivoted in movable finger, FIG. 30 a sectional view of this holding apparatus without the movable finger, FIG. 31 the movable finger in a side view, FIG. 32 a view of this holding apparatus from the front, with pivoted out movable finger, FIG. 33 a sectional, illustration of this holding apparatus with pivoted in finger, for explaining the three point support, FIG. 34 an eighth exemplary embodiment of a holding apparatus in accordance with the invention in an exploded view, FIG. 35 the exemplary embodiment in accordance with FIG. 34 in side view, FIG. 36 an exemplary embodiment of the cover of a holding apparatus in accordance with the invention in sectional representation, FIG. 37 a further exemplary embodiment of the cover of a holding apparatus in accordance with the invention in sectional representation, FIG. 38 the exemplary embodiment of the cover in accordance with FIG. 37 in a view from the front, FIG. 39 a further exemplary embodiment of the cover of a holding apparatus in accordance with the invention in sectional representation, FIG. 40 the exemplary embodiment of the cover in accordance with FIG. 39 in a view from the front, FIG. 41 a further exemplary embodiment of the cover of a holding apparatus in accordance with the invention in sectional representation, FIG. 42 the exemplary embodiment of the cover in accordance with FIG. 41 in a view from the front and FIG. 43 the exemplary embodiment of the cover in accordance with FIG. 41 in a side view.

Although in the following only hook-like exemplary embodiments for the securing of the holding apparatus at the vertebra are shown, the explanations naturally also hold in an analogous manner for other kinds of securing of the holding apparatus, such as e.g. for securings by means of (pedicle) screws. Furthermore, the individual holding apparatuses, which are described in the following for posterior accesses to the spinal column, can naturally also be modified in such a manner that they can be used for anterior accesses.

In FIGS. 2 to 4 a first exemplary embodiment of a holding apparatus in accordance with the invention is shown. One recognizes here in particular a hook base body 1 which has a mount 2 in the upper part which serves for receiving a bar 3 (in the figures only a section of the bar is in each case illustrated). Furthermore, one recognizes a cylindrical clip 4 which is sickle shaped in cross-section and which is designed in such a manner that it enters into a snap connection with the bar 3. For this the clip 4 reaches around the bar 3 by more than half of the periphery and is elastic up to a certain extent. The mount 2 has a corresponding cylindrical cut-out 20 which is substantially sickle shaped and which is slightly larger than the clip 4 so that the clip 4, which is snapped onto the bar, can be introduced into the cut-out 20 in the mount 2, that is, can be pushed in, or the holding apparatus can be pushed over the clip 4 respectively. Furthermore, the mount 2 also has a cut-out 21 in which the bar 3 comes to lie.

Once the clip 4 has been introduced into the cut-out 20 of the mount 2 or the holding apparatus has been pushed over the clip 4 which has been snapped onto the bar 3 respectively, then the bar 3 can no longer escape out of the cut-out 20 or 21 respectively, even if the spinal column attempts to cause a restoring movement of this kind. A temporary fixing has taken place, which however still permits a displacement of the holding apparatus on the bar in the direction of the bar 3.

The clip 4 is furthermore provided with a through-going threaded bore 40 for a clamping screw 5. When this clamping screw 5 is screwed through the threaded bore 40 it presses the bar 3 firmly into the cut-out 21, whereas the sickle shaped clip 4 is pressed on at the inner wall of the sickle shaped cut-out 20 of the mount 2. Once this has taken place, the holding apparatus can no longer be displaced, but rather is rigidly connected to the bar 3.

In this the individual elements are designed here in such a manner that a three point support at the points P1, P2, P3 comes about. In this exemplary embodiment one support point P1 comes to lie in the region of the cut-out 21, whereas a further support point P2 comes to lie in the region of the sickle shaped clip 4. The third support point P3 is formed by the clamping screw 5. Three point supports of this kind are known per se and effect a reliable support of the bar 3.

A further exemplary embodiment of a holding apparatus in accordance with the invention can be recognized in FIGS. 5–8. From the exploded view in FIG. 5 one recognizes the hook base body 1a with the mount 2a, the bar 3a and a cover 6a. The cover 6a has a circumferential flange 60a which projects from the cover. Two cut-outs 61a for the bar 3a are provided in the flange. Projections 62a and depressions 63a are provided on the inner wall of the flange 60a and enter into a snap connection with corresponding projections 22a and depressions 23a on the outer wall of the mount 2a. When mounting the cover 6a the lower projection in the cover can for example first be pushed only over the upper projection on the outer wall of the mount so that it snaps in in this position. The bar 3a is then already captured in such a manner that it can no longer escape upwardly out of the mount. At the same time naturally the holding apparatus (and thus naturally also the vertebra, to which the holding apparatus is connected) is still movable in the direction of the bar 3a and is also still somewhat tiltable in the axial direction, which facilitates the handling for the operating surgeon under certain circumstances. Alternatively, the lower projection in the cover 6a can also be pushed over the lower projection on the outer wall of the mount, which results in lower axial tiltability, but still ensures the displaceability of the holding apparatus relative to the bar 3a.

Finally, the clamping screw 5a is screwed through the threaded bore 40a which is provided in the cover 6a. As soon as the clamping screw 5a is supported on the bar 3a it pulls the cover 6a upwardly, with the projections 62a and the depressions 63a then being supported on the corresponding projections 22a and depressions 23a of the mount 2a. In this way the holding apparatus is then rigidly connected to the bar 3a (FIG. 6, FIG. 7).

In FIG. 8, finally, one recognizes the three point support at the support points P1a, P2a, P3a. A three point support of this kind is conventional; for this the cut-out 21a in the mount 2a must have a radius in the lower region which is less than the radius of the bar 3a. In the regions adjoining at this region the radius of the cut-out must then be greater than the radius of the bar 3a. This preferably takes place with a tangential transition. This kind of three point support is however already known per se.

Common to the exemplary embodiments in accordance with FIGS. 2 to 4 and those in accordance with FIGS. 5 to 8 is that the temporary retention of the bar 3 or 3a respectively comprise an element which enters into a snap connection with the bar or with the holding apparatus. There are naturally alternatives to this kind of connection, as will be described in the following.

A further exemplary embodiment of the holding apparatus in accordance with the invention is illustrated in FIGS. 9 to 13. A hook base body 1b with a mount 2b in which the bar 3b comes to lie can be recognized. Furthermore, one recognizes a cover 6b which can be pushed on and which enters into a connection of the manner of a bayonet lock after being pushed on. For this the cover 6b has two flanges 60b which project from the cover, which in each case have a support surface 61b and which cooperate with a corresponding support surface 21b, so that during the pushing on of the cover 6b, the support surface 21b at the respective flange 61b is guided along the respective support surface 21b at the mount 2b. The cover 6b furthermore has at that end of the support surface 61b which faces the inner end surface of the cover a projection 62b which extends in the peripheral direction. Accordingly, a projection 22b which projects outwardly from the mount 2b is provided at the upper end of the mount 2b. Once the cover 6b has been pushed along the support surface 21b onto the mount 2b up to the end of the support surface 61b, then it can be rotated relative to the hook base body 1b or the mount 2b respectively. In this the projection 62b of the cover 6b engages in the manner of a bayonet lock behind the projection 22b which projects outwardly from the mount 2b. The bar 3b is then captured and can no longer escape upwardly out of the mount; at the same time the holding apparatus however still remains displaceable on the bar 3a in the axial direction. The final rigid fixing of the holding apparatus to the bar 3b takes place in such a manner that the clamping screw 5b, which is passed through the threaded bore 40b, presses the bar 3b into the mount and in so doing draws the cover 6b upwardly. The latter is supported via the cooperating projections 62b and 22b so that the holding apparatus is then rigidly connected to the bar 3b.

In FIG. 13 one finally also recognizes the three point support at the support points P1b, P2b, P3b. A three point support of this kind is conventional; for this the cut-out in the mount 2b must have a radius in the lower region which is less than the radius of the bar 3b. In the regions adjoining at this region the radius of the cut-out must then be greater than the radius of the bar 3b. This preferably takes place with a tangential transition. This kind of three point support is however already known per se.

FIGS. 14 to 17 show a further exemplary embodiment of the holding apparatus in accordance with the invention. One recognizes the hook base body 1c, the mount 2c for the bar 3c, the cover 6c and the clamping screw 5c, which can be screwed completely through the threaded bore 40c. The cover 6c has two flanges 60c which project from the cover and which in each case have an inwardly projecting pin 61c on their inner wall. In the wall of the mount 2c a groove 21c is provided which first extends substantially in the axial direction and then substantially in the peripheral direction. At the upper end the groove 21c also has two chamfers 210c which facilitate the introduction of the pin 61c into the groove 21c. The cover 6c is pushed in the axial direction onto the hook base body 1c or the mount 2c respectively, with the pins 61c sliding into the groove 21c in the axial direction. Once the cover 6c has been pushed forward in the axial direction to such an extent that the pins 61c have arrived at the end of the part of the groove 21c which extends in the axial direction, the cover 6c can be rotated relative to the hook base body 1c or relative to the mount 2c respectively. Through this the bar 3c is captured in the mount 2c and can not slide upwardly out of the mount 2c. Nevertheless however the holding apparatus remains displaceable relative to the bar in the axial direction—in relation to the bar. Then the clamping screw 5c is screwed completely through the threaded bore 40c and presses the bar 3c into the mount 2c. In this the cover 6c is drawn upwards, with the pins 61c being supported in the groove 21c (in that part of the groove 21c which extends in the peripheral direction). Through this the holding apparatus is rigidly connected with the bar 3c.

In FIG. 17 one finally also recognizes the three point support at the support points P1c, P2c, P3c. A three point support of this kind is conventional; for this the cut-out in the mount 2c must have a radius in the lower region which is less than the radius of the bar 3c. In the regions adjoining at this region the radius of the cut-out must then be greater than the radius of the bar 3c. This preferably takes place with a tangential transition. This kind of three point support is however already known per se.

Common to the exemplary embodiments in accordance with FIGS. 9 to 13 and those in accordance with FIGS. 14 to 17 is that the means for retaining the bar 3b or 3c respectively in the mount 2b or 2c respectively comprise a cover 6b or 6c respectively which is designed in such a manner that it engages in a connection of the manner of a bayonet lock with corresponding means of the holding apparatus. Alternatives to this are naturally possible and will be described in the following.

FIGS. 18 to 21 show a further exemplary embodiment of the holding apparatus in accordance with the invention. One recognizes the hook base body 1d, the mount 2d for the bar 3d and a cover 6d which has a threaded bore 40d through which a clamping screw 5d can be completely screwed. One further recognizes that the wall of the mount 2d is designed to be elastically deformable in that end region which faces the cover 6d (that is, the upper) and has projections 22d. Likewise the cover 6d has projections 62d (namely at the inside) which can be brought into engagement with the projections 22d of the mount. First the hook base body 1d is brought into engagement with the bar 3d in such a manner that the bar 3d is snapped in into the mount 2d. Through this the bar 3d is captured and can no longer slide out of the mount 2d in the axial direction (that is, upwardly). Then the cover 6d is pushed on. The latter can be pushed onto the mount 2d without hindrance. The bar, which is snapped into the mount, is still displaceable in the axial direction—in relation to the bar. The clamping screw 5d can already be screwed loosely into the threaded bore 40d or else also be screwed in only afterwards. For the rigid securing of the holding apparatus at the bar 3d the clamping screw 5d is now screwed in. In this the elastic end regions of the walls with the projections 22d deform outwardly and enter in this way into engagement with the projections 62d inwardly at the cover (FIG. 20). In this way the holding apparatus is then rigidly connected to the bar 3d.

In FIG. 21 one finally also recognizes the three point support at the support points P1d, P2d, P3d. A three point support of this kind is conventional; for this the cut-out in the mount 2d must have a radius in the lower region which is less than the radius of the bar 3d. In the regions adjoining at this region the radius of the cut-out must then be greater than the radius of the bar 3d. This preferably takes place with a tangential transition. This kind of three point support is however already known per se.

Finally, two further exemplary embodiments of a holding apparatus in accordance with the invention are described in FIGS. 22 to 27 and in FIGS. 28 to 33. Both have a hook base body 1e or if respectively which has a mount 2e or 2f respectively. At the mount 2e or 2f respectively two hook-like, stationary fingers 21e and 22e or, respectively, 21f and 22f are formed in each case which define between themselves a cut-out 23e or 23f respectively. A pivotally movable finger 24e or 24f respectively is in each case arranged in this cut-out 23e or 23f respectively. In the hook-like, stationary fingers 21e and 22e or, respectively, 21f and 22f a pin 210e and 220e or, respectively, 210f and 220f is provided at the respective surface which points to the movable finger. These pins engage in each case into a corresponding cut-out 240e or 240f respectively (FIG. 25 and FIG. 31 respectively) which is provided at the movable finger 24e or 24f respectively and indeed in each case in the corresponding surface which points to the respective stationary finger. The pins 210e and 220e or, respectively, 210f and 220f can in this situation be pressed in and/or welded or stapled on respectively.

The pivotal finger 24e or 24f respectively is furthermore provided with an extension 241e or 241f respectively which projects outwardly beyond the cut-out 23e or 23f respectively. This extension 241e or 241f respectively is provided with an outer thread onto which a nut 25e or 25f respectively can be screwed. In the opened position (FIG. 26 or FIG. 32 respectively) the bar 3e or 3f respectively can be introduced into the mount 2e or 2f respectively and then the pivotal finger 24e or 24f respectively can be pivoted. Through this the bar 3e or 3f respectively is captured since the pins slide in into an undercutting in the respective cut-out 240e or 240f respectively of the movable finger 24e or 24f respectively. At the same time the holding apparatus is still movable in the axial direction—in relation to the bar 3e or 3f respectively. If now the nut 25e or 25f respectively is tightened, then the bar 3e or 3f respectively is firmly pressed by the movable finger 24e or 24f respectively against the bar 3e or 3f respectively, which in turn is firmly pressed into the mount 2e or 2f respectively. In this the nut 25e or 25f respectively is in turn supported on the two stationary hook-like fingers 21*e* and 22*e* or, respectively, 21*f* and 22*f*.

In FIGS. 27 and 33 respectively one also recognizes the three point support with the support points P1*e*, P2*e*, P3*e* and, respectively, P1*f*, P2*f*, P3*f*. For this the mount 2*e* or 2*f* respectively has a radius in the left region which is less than the radius of the bar 3*e* or 3*f* respectively, and in the regions adjoining at this region a radius which is greater than the radius of the bar 3*e* or 3*f* respectively. This preferably takes place with a tangential transition. This kind of three point support is however known per se.

FIGS. 34 and 35 show a further exemplary embodiment of the holding apparatus in accordance with the invention. This exemplary embodiment is similar in principle to the exemplary embodiment which was explained with reference to FIGS. 14 to 17. In the exemplary embodiment which is shown in FIG. 34 and in FIG. 35 respectively one recognizes the hook base body 1*g*, the mount 2*g* for the bar 3*g*, the cover 6*g* and the clamping screw 5*g*, which can be screwed completely through the threaded bore 40*g*. At the hook base body 1*g* or at the mount 2*g* respectively, pins 21*g* are provided which project outwardly from the outer wall of the mount 2*g*. The cover 6*g* has two flanges 60*g* which project from the cover and in which in each case a groove 61*g* is provided. The groove 61*g* extends at first substantially in the axial direction and then substantially in the peripheral direction. At its lower end the groove 61*g* has two chamfers 610*g* which facilitate the introduction of the pins 21*g* into the groove 61*g*. The cover 6*g* is pushed on in the axial direction onto the hook base body 1*g* or onto the mount 2*g* respectively, with the pins 21*g* sliding in into the groove 61*g* in the axial direction. Once the cover 6*g* has been pushed forward in the axial direction to such an extent that the pins 21*g* have arrived at the part of the groove 61*g* which extends in the axial direction, the cover 6*g* can be rotated with respect to the hook base body 1*g* or relative to the mount 2*g* respectively. The bar 3*g* is thereby captured in the mount 2*g* and can not slide out upwardly out of the mount 2*g*. The holding apparatus nevertheless remains displaceable relative to the bar in the axial direction with respect to the bar. Then the clamping screw 5*g* is screwed through the threaded bore 40*g* and presses in the bar 3*g* into the mount 2*g*. In this the cover 6*g* is drawn upwardly, with the pins 21*g* being supported in the groove 61*g* (in that portion of the groove 61*g* which extends in the peripheral direction). The holding apparatus is thereby rigidly connected to the bar 3*b*. Here as well the three-point support of the bar 3*g* which was already mentioned above with reference to the preceding exemplary embodiments takes place.

FIGS. 36 to 43 show further exemplary embodiments of the cover of the holding apparatus in accordance with the invention which are related from the point of view of the principle to the exemplary embodiment in accordance with FIGS. 5 to 8, namely in such a manner that the cover enters into a snap connection with the hook base body or with the mount respectively. The hook base body can in principle have the appearance which is illustrated in FIG. 8 and is therefore not represented further.

In FIG. 36 an exemplary embodiment of a cover 6*h* is illustrated which has a circumferential flange 60*h* which projects from the cover, in which a threaded bore 40*h* for a clamping screw is provided. Two cutouts 61*h* for the bar are provided in the flange. On the inner wall of the flange 60*h* projections 62*h* and depressions 63*h* are provided which enter into a snap connection with corresponding projections and depressions respectively of the hook base body. During the mounting of the cover 6*h* the latter is pushed in the axial direction over the projections at the hook base body and snaps in. The flange 60*h* must have a certain flexibility; otherwise it can not be pushed over the projections at the hook base body. In order to increase the elasticity of the flange 60*h*, a circumferential cut-out 600*h* which reduces the wall thickness of the flange 60*h* and thus increases the required elasticity of the cover 6*h* is provided in the inner wall of the cover near the cover base.

In a further development of the cover the elasticity of the flanges 60*i* can be increased still further through a circumferential groove 610*i* on the outer wall of the cover 6*i*, as is illustrated in FIG. 37 and in FIG. 38, in which the threaded bore 40*i* for a clamping screw and the cut-out 61*i* for the bar can also be recognized.

In FIG. 39 and FIG. 40 a further exemplary embodiment of the cover 6*j* with the threaded bore 40*j* for a clamping screw is shown in which not two but rather four flanges 60*j* and accordingly also four cut-outs for the bar are provided. Since not two, but rather four flanges 60*j* of this kind and accordingly also four cut-outs 61*j* are provided for the bar, the flanges 60*j* become smaller in their extent in the peripheral direction and thereby also more elastic.

Furthermore, in this exemplary embodiment as well a circumferential cut-out 600*j* is provided on the inner wall near the cover base, through which the elasticity of the individual flanges 60*j* is still further increased. The cut-outs 61*j* between the flanges 60*j* all have the same width b, so that in a bar with corresponding diameter the cover 6*j* can be pushed on onto the hook base body (not illustrated) in four different angular positions in order to enter into the snap connection.

Finally, in FIG. 41, FIG. 42 and FIG. 43 a further exemplary embodiment of the cover 6*k* with a threaded bore 40*k* for a clamping screw is illustrated. This exemplary embodiment of the cover likewise has four flanges 60*k*, between which cut-outs 61*k* for the bar are provided. As can be recognized especially from FIG. 42 and FIG. 43, however, the cutouts 61*k* do not have the same width; but rather two mutually oppositely lying cut-outs 61*k* have a first width b1 (FIG. 42) whereas the other two mutually oppositely lying cut-outs 61*k* have a second width b2 (FIG. 43). This increases on the one hand the elasticity of individual flanges 60*k*; on the other hand it is also possible to use hook base bodies which admittedly have a uniform outer diameter of the mount, but in which however the inner dimensions of the mount can vary, so that depending on the inner dimensions of the mount of the hook base body either a bar can be received to which the width b1 of the cut-out 61*k* of the cover 6*j* corresponds or a bar to which the width b2 of the cut-out 61*k* of the cover 6*j* corresponds. Furthermore, here as well a cut-out 600*k* which increases the elasticity of the individual flanges 60*k* is provided on the inner wall of the cover 6*j* near the cover base. As has already been mentioned initially the holding apparatus in accordance with the invention, which has been explained above with reference to different exemplary embodiments, is particularly suitable for the indication field of scoliosis. It is however also suitable for other indication fields, such as cyphosis and lordosis. The holding apparatus can likewise be modified in such a manner that it can be used for anterior accesses to the spinal column. Finally, the holding apparatus can also be modified in such a manner that it can be used for the transverse stabilization (between the two bars) so that a torsion of the upper torso can not cause a movement of the two bars relative to one another.

What is claimed is:

1. Holding apparatus for the spinal column, said holding apparatus having means for securing to a vertebra and having a mount for a bar which is provided at a side of the holding apparatus which faces away from the securing means, as well as comprising means for producing a rigid connection of the holding apparatus to the bar which is located in the mount, means for retaining the bar in the mount which are executed in such a manner and can be brought into connection with the holding apparatus in a manner to temporarily retain in the mount a bar which is introduced into the mount until the holding apparatus is fixed to the bar with the help of the means for producing the rigid connection, the means for retaining the bar comprising a sickle-shaped finger which is pivotally arranged in a cut-out between first and second stationary fingers formed in a hook-like manner at the mount, with in each case a pin which points to the movable finger being provided on a respective surface of the stationary hook-like finger which points to the movable finger and which engages into a corresponding cut-out provided at the movable finger in a respective surface pointing to the stationary finger, the movable finger having an extension which projects outwardly beyond the cut-out and which is provided with a thread onto which a nut can be screwed.

2. Holding apparatus in accordance with claim 1, wherein the mount for the bar is configured so that the means for retaining the bar can be brought into connection with the mount for the bar.

3. Holding apparatus in accordance with claim 1, wherein the mount for the bar and the means for producing the rigid connection of the holding apparatus to the bar are executed in such a manner that they form a three-point support.

* * * * *